US012799452B2

(12) United States Patent
Duboux et al.

(10) Patent No.: US 12,799,452 B2
(45) Date of Patent: Nov. 17, 2026

(54) SERPIN PRODUCTION

(71) Applicant: SOCIETE DES PRODUITS NESTLE S.A., Vevey (CH)

(72) Inventors: Stephane Duboux, St-Prex (CH); Peter Duncan, Epalinges (CH); Mireille Golliard, Lausanne (CH); Michiel Kleerebezem, Wageningen (NL)

(73) Assignee: Societe des Produits Nestle S.A., Vevey (CH)

( * ) Notice: Subject to any disclaimer, the term of this patent is extended or adjusted under 35 U.S.C. 154(b) by 356 days.

(21) Appl. No.: 17/597,304

(22) PCT Filed: Jun. 30, 2020

(86) PCT No.: PCT/EP2020/068399
§ 371 (c)(1),
(2) Date: Dec. 31, 2021

(87) PCT Pub. No.: WO2021/001367
PCT Pub. Date: Jan. 7, 2021

(65) Prior Publication Data
US 2023/0220327 A1 Jul. 13, 2023

(30) Foreign Application Priority Data
Jul. 1, 2019 (EP) .................................... 19183648

(51) Int. Cl.
*C12N 1/20* (2026.01)

(52) U.S. Cl.
CPC ............ *C12N 1/20* (2013.01); *C12N 2500/34* (2013.01)

(58) Field of Classification Search
CPC .............................. C12N 1/20; C12N 2500/34
See application file for complete search history.

(56) References Cited

U.S. PATENT DOCUMENTS

2011/0177034 A1 7/2011 Kildsgaard et al.

FOREIGN PATENT DOCUMENTS

| | | | | |
|---|---|---|---|---|
| BR | 112020010929 A2 | 11/2020 | | |
| CN | 106072658 A | 11/2016 | | |
| EP | 2289527 | 3/2011 | | |
| JP | 2011507540 A | 3/2011 | | |
| JP | 2012520325 A | 9/2012 | | |
| JP | 2019097544 A | 6/2019 | | |
| WO | 2007093619 | 8/2007 | | |
| WO | 2019025637 | 2/2019 | | |
| WO | WO-2019025637 A1 * | 2/2019 | .......... | A23L 33/135 |
| WO | 2019129808 | 7/2019 | | |

OTHER PUBLICATIONS

Rattanaprasert, 2015. Efficacy of Galactooliosaccharide (GOS) and/or Rhamnose-Based Synbiotics in Enhancing Ecological Performance of Lactobacillus reuteri in the Human Gut and Characterization of Its GOS Metabolic System. https://digitalcommons.unl.edu/foodscidiss/62/ (Year: 2015).*
McCarville JL, et al., A Commensal Bifidobacterium longum Strain Prevents Gluten-Related Immunopathology in Mice through Expression of a Serine Protease Inhibitor. Appl Environ Microbiol. Sep. 15, 2017;83(19):e01323-17. doi: 10.1128/AEM.01323-17. PMID: 28778891; PMCID: PMC5601352. (Year: 2017).*
Hsu CA, Yu RC, Chou CC. Production of beta-galactosidase by Bifidobacteria as influenced by various culture conditions. Int J Food Microbiol. Oct. 15, 2005;104(2): 197-206. doi: 10.1016/j.ijfoodmicro.2005.02.010. PMID: 15985305. (Year: 2005).*
He et al., "Proteomic Analysis of Bifidobacteria Longum Strain NCC2705 Grown on Lactose and Glucose", Acta Microbiologica Sinica, vol. 48, Issue No. 11, Nov. 4, 2008, pp. 1451-1458.
Office Action Received for Application No. CN202080047233.0, mailed on Aug. 26, 2023, 08 Pages of Official Copy.
Turroni et al. "Characterization of the Serpin-Encoding Gene of Bifidobacterium breve 210B" Applied and Environmental Microbiology, May 2010, vol. 76, No. 10, pp. 3206-3219.
Mccarville et al. "A Commensal Bifidobacterium longum Strain Prevents Gluten-Related Immunopathology in Mice through Expression of a Serine Protease Inhibitor" Applied and Environmental Microbiology, Oct. 2017, vol. 83, issue 19, 13 pages.
Parche et al. "Sugar Transport Systems of Bifidobacterium longum NCC2705" Journal of Molecular Microbiology and Biotechnology, 2007, vol. 12, pp. 9-19.
Japanese Office Action for Appl No. 2021-576390 dated Jun. 25, 2024, 8 pages.
Brazilian Office Action for Appl No. BR112021025362-9—dated Apr. 1, 2026, 4 pages.

* cited by examiner

*Primary Examiner* — Louise W Humphrey
*Assistant Examiner* — Rachel Emily Martin
(74) *Attorney, Agent, or Firm* — K&L Gates LLP

(57) ABSTRACT

Use of galactose or a galactooligosaccharide, for increasing serpin protein production in *Bifidobacterium longum* subsp. *longum*.

13 Claims, 4 Drawing Sheets

| | | | | | | | |
|---|---|---|---|---|---|---|---|
| GOS | 0.9 | 0.7 | 0.5 | 0.6 | 0.3 | 0.5 | 0.25 |
| other (glu, lac) | 0.1 | 0.3 | 0.2 | 0.4 | 0.2 | 0.4 | 0.2 |

SERPIN PRODUCTION

CROSS REFERENCE TO RELATED APPLICATIONS

The present application is a National Stage of International Application No. PCT/EP2020/068399, filed on Jun. 30, 2020. which claims priority to European Patent Application No. 19183648.5, filed on Jul. 1, 2019, the entire contents of which are being incorporated herein by reference.

FIELD OF THE INVENTION

The present invention relates to bacteria expressing serpin, methods for increasing serpin production in bacteria and uses thereof.

BACKGROUND TO THE INVENTION

Gluten-related disorders comprise all diseases triggered by gluten. They include, amongst other pathophysiology, celiac disease and non-celiac gluten sensitivity. Currently, the incidence of a wide spectrum of gluten-related disorders is growing all around the world, especially for celiac disease and non-celiac gluten sensitivity. Both diseases are triggered by ingestion of gluten. Both innate and adaptive immunity are implicated in celiac disease while innate immunity is implicated in non-celiac gluten sensitivity.

A life-long gluten-free diet is the gold standard treatment for celiac disease and non-celiac gluten sensitivity patients, although it may have some limitations on the extraintestinal manifestations of the disease (Sedghizadeh et al., 2002, Oral Surgery, Oral Medicine, Oral Pathology, Oral Radiology, and Endodontology, 94(4), 474-478). It has been shown that following a strict gluten free diet is very difficult as low level cross-contaminations are difficult to avoid and may happen through the whole food production chain, from grains growth to manufacturing processing (Mitchison et al., 1991, Gut, 32(3), 260-265). Furthermore, it has been described that up to 3 g of hidden gluten might be consumed daily under a strict gluten free diet (Aziz et al., 2014, The American journal of gastroenterology, 109(9), 1498).

Celiac disease is prevalent especially in the United States and Europe where around 1% of subjects had positive antibody tests (Dube et al., 2005, Gastroenterology, 128(4), S57-S67). It is a complex disorder which arises from a complicated interaction among various immunologic, genetic, and environmental factors (Alaedini & Green, 2005). It is triggered by the digestion of wheat gluten and other related cereal proteins such as rye and barley proteins. Symptoms linked with celiac disease are growth retardation, irritability and pubertal delay in children and many gastrointestinal symptoms such as discomfort, diarrhoea, occult stool, steatorrhea and flatulence, (Dube et al., 2005; Sedghizadeh et al., 2002).

Non-celiac gluten sensitivity (also named non-celiac wheat sensitivity) is an emerging condition. It is defined as a clinical entity induced by the ingestion of gluten leading to intestinal and/or extraintestinal symptoms which could be improved by removing the gluten-containing foodstuff from the diet (Lundin & Alaedini, 2012). In addition to gliadin (the main cytotoxic antigen of gluten), other proteins/peptides present in gluten and gluten-containing cereals (wheat, rye, barley, and their derivatives) may play a role in the development of symptoms. Non-celiac gluten sensitivity is the most common syndrome of gluten-related disorders with prevalence rates between 0.5-13% in the general population (on average 5%) (Catassi et al., 2013, Nutrients, 5(10), 3839-3853).

Serine protease inhibitors (serpin) are a superfamily of proteins found in eukaryotes (Gettins, 2002, Chemical reviews, 102(12), 4751-4804) and prokaryotes (Kantyka et al., Biochimie, 92(11), 1644-1656).

Recently, human serine protease inhibitors have been shown to play an important role in gluten related disorders. Elafin is human serine protease inhibitor which shows potent inhibitory capacity against various forms of elastases and proteinase (Ying & Simon, 1993, Biochemistry, 32(7), 1866-1874). Elafin is expressed throughout the epithelium of the gastrointestinal tract and its expression and induction is decreased in patients with inflammatory bowel disease and celiac disease (Baranger, Zani, Labas, Dallet-Choisy, & Moreau, 2011; Motta et al., 2012). Recently, elafin has been identified as a substrate for the cross-linking activity of transglutaminase 2 (TG2) (Baranger et al., 2011, PloS one, 6(6), e20976; Motta et al., Science translational medicine, 4(158), 158ra144-158ra144). In-vitro data shows that the addition of elafin moderately inhibits transglutaminase 2 (TG2) thus inhibiting the deamidation of the digestion-resistant 33-mer gliadin 20 peptide, which is one of the potential triggers of the adaptive immune response in celiac disease (McCarville et al. 2015, Current opinion in pharmacology, 25, 7-12).

Delivery of elafin, produced by a recombinant *Lactococcus lactis* has been shown to reduce gluten-induced pathology and normalise intestine inflammation in a mouse model of gluten sensitivity (Galipeau et al., 2014, The American journal of gastroenterology, 109(5), 748-756). However, this proposed therapy is based on a genetically modified microorganism (GMO) and is therefore not compatible with a food application, as consumer acceptance of GMO is very low.

More recently, serpins have been reported in prokaryotes. In silico analysis revealed the presence of genes encoding serpin-like proteins in different *Bifidobacterium* species, particularly in bacteria of the species *Bifidobacterium longum* subsp *longum*. The protein encoded by *B. longum* subsp *longum* (named *B. longum*) NCC 2705 displayed similar antiprotease activity to those of human serpin (Ivanov et al 2006, Journal of Biological Chemistry, 281 (25), 17246-17252).

*B. longum* NCC 2705 was deposited with the Institute Pasteur according to the Budapest Treaty on 29 Jan. 2001 receiving the deposit no. CNCM 1-2618.

It has recently been shown that *B. longum* NCC 2705 (CNCM 1-2618), through its serpin production can improve gluten induced pathophysiology in a mouse model of gluten sensitivity, showing its potential as a solution for gluten related disorders (McCarville et al., 2017, Appl. Envoron. Microbiol. Vol. 83, no. 19, e01323-17).

SUMMARY OF THE INVENTION

The present inventors have surprisingly found that galactose and galactooligosacharrides (GOS) can increase the production of serpin when added to the growth medium of bacteria of the species *Bifidobacterium longum* subsp *longum*.

Accordingly, in a first aspect of the present invention, there is provided use of galactose or a galactooligosaccharide (GOS), or combinations thereof, for increasing serpin production in a *Bifidobacterium longum* subsp *longum*.

In another aspect of the present invention, there is provided a method of increasing serpin production in a bacteria of the species *Bifidobacterium longum* subsp *longum*, wherein said method comprises growing *Bifidobacterium longum* subsp *longum* in a culture medium, characterised in that said culture medium comprises galactose or a galactooligosacharride (GOS), or combinations thereof.

According to another aspect of the present invention, there is provided a bacteria of the species *Bifidobacterium longum* subsp *longum* produced by a method of growing the *Bifidobacterium longum* subsp *longum* in a culture medium, characterised in that said culture medium comprises galactose or a GOS, or combinations thereof.

The *Bifidobacterium longum* subsp *longum* produced according to the present invention is associated with increased serpin protein levels relative to the same *Bifidobacterium* longumsubsp *longum* strain grown in the absence of galactose or GOS, or combinations thereof.

According to the present invention, the *Bifidobacterium longum* subsp *longum* may be cultured in a medium comprising the galactose or GOS, or combinations thereof, at a concentration of, for example, 0.02 to 5 wt %, preferably 0.05 to 2 wt %.

For example, the *B. longum* strain CNCM 1-2618 may be cultured in a medium comprising the galactose or GOS, or combinations thereof, at a concentration of 0.02 to 5 wt %, 0.05 to 2 wt %, 0.1 to 1.5 wt or about 1%.

According to another aspect of the present invention, there is provided a composition comprising a *Bifidobacterium longum* subsp *longum* produced according to the method described herein.

In one embodiment, the composition is a food, a medical food, a tube feed, or a nutritional supplement.

In one embodiment, the food is selected from milk, yoghurt, curd, cheese, fermented milks, milk based fermented products, rice based products, milk based powders, infant formulae and pet food.

In one embodiment, the composition is a pharmaceutical composition wherein the pharmaceutical composition comprises one or more pharmaceutically acceptable carriers, diluents and/or excipients.

According to another aspect of the present invention there is provided a *Bifidobacterium longum* subsp *longum* produced according to the method described herein, or a composition comprising said *Bifidobacterium longum* subsp *longum*, for use in the treatment or prevention of conditions related to gluten sensitivity or involving the reduced activity of serine protease inhibitors.

According to another aspect of the present invention there is provided a *Bifidobacterium longum* subsp *longum* produced according to the method described herein, or a composition comprising said *Bifidobacterium longum* subsp *longum*, for use in the treatment or prevention of a gluten related disorder.

According to an aspect of the present invention there is provided a *Bifidobacterium longum* subsp *longum* produced according to the method described herein, or a composition comprising said *Bifidobacterium longum* subsp *longum*, for use in the treatment or prevention of, celiac disease, non-celiac gluten sensitivity, gluten ataxia, dermatitis herpetiformis or wheat allergy.

According to another aspect of the present invention there is provided a *Bifidobacterium longum* subsp *longum* produced according to the method described herein, or a composition comprising said *Bifidobacterium longum* subsp *longum*, for use in the treatment or prevention of inflammatory bowel disease.

The *Bifidobacterium longum* subsp *longum* may be any *Bifidobacterium longum* subsp *longum* strain. In some preferred embodiments the *Bifidobacterium longum* subsp *longum* strain may be selected from *Bifidobacterium longum* subsp *longum* strain CNCM 1-2169, *Bifidobacterium longum* subsp *longum* strain CNCM 1-2171, *Bifidobacterium longum* subsp *longum* strain ATCC BAA-999, *Bifidobacterium longum* subsp *longum* strain ATCC 15708, *Bifidobacterium longum* subsp *longum* strain DSM 20097, *Bifidobacterium longum* subsp *longum* strain NCIMB 8809, *Bifidobacterium longum* subsp *longum* strain CNCM 1-2618 (NCC 2705), *Bifidobacterium longum* subsp *longum* strain CNCM 1-2170, *Bifidobacterium longum* subsp *longum* strain ATCC 15707 (T), or a combination thereof, in particular *B. longum* CNCM 1-2618 (NCC 2705).

It will also be appreciated that the galactose and/or GOS may also increase the production of 15 serpin in *Bifidobacterium longum* subsp *longum* in vivo when the galactose or GOS, or a combination thereof, is administered in combination with the *Bifidobacterium longum* subsp *longum.*

Thus, according to another aspect of the present invention there is also provided a combination of (i) a *Bifidobacterium longum* subsp *longum* and (ii) galactose or GOS, or combinations thereof.

According to another aspect of the present invention there is also provided a combination of (i) a *Bifidobacterium longum* subsp *longum* and (ii) galactose or GOS, or a combination thereof, for use in the treatment or prevention of a condition related to gluten sensitivity or a condition linked to reduced levels of serine protease inhibitors.

In one embodiment, the combination is a combination of *B. longum* strain CNCM 1-2618 and galactose.

According to another aspect of the present invention there is also provided *Bifidobacterium longum* subsp *longum* for use in the treatment or prevention of a condition related to gluten sensitivity or a condition linked to reduced levels of serine protease inhibitors, wherein the *Bifidobacterium longum* subsp *longum* is administered in combination with galactose or GOS, or a combination thereof.

According to another aspect of the present invention there is provided galactose or GOS, or a combination thereof for use in the treatment or prevention of a condition related to gluten sensitivity, or a condition linked to reduced levels of serine protease inhibitors, wherein the galactose or GOS, or a combination thereof, is administered in combination with *Bifidobacterium longum* subsp *longum.*

In some embodiments the *Bifidobacterium longum* subsp *longum* may be selected from *Bifidobacterium longum* subsp *longum* strain CNCM 1-2169, *Bifidobacterium longum* subsp *longum* strain CNCM 1-2171, *Bifidobacterium longum* subsp *longum* strain ATCC BAA-999, *Bifidobacterium longum* subsp *longum* strain ATCC 15708, *Bifidobacterium longum* subsp *longum* strain DSM 20097, *Bifidobacterium longum* subsp *longum* strain NCIMB 8809, *Bifidobacterium longum* subsp *longum* strain CNCM 1-2618 (NCC 2705), *Bifidobacterium longum* subsp *longum* strain CNCM 1-2170, *Bifidobacterium longum* subsp *longum* strain ATCC 15707 (T), or a combination thereof.

In some preferred embodiments, the *Bifidobacterium longum* subsp *longum* may be selected from *Bifidobacterium longum* subsp *longum* strain CNCM 1-2169, *Bifidobacterium longum* subsp *longum* strain CNCM 1-2171, *Bifidobacterium longum* subsp *longum* strain ATCC 15708, *Bifidobacterium longum* subsp *longum* strain DSM 20097, *Bifidobacterium longum* subsp *longum* strain NCIMB 8809, *Bifidobacterium longum* subsp *longum* strain CNCM 1-2618 (NCC 2705), *Bifidobacterium longum* subsp *longum* strain CNCM 1-2170, *Bifidobacterium longum* subsp *longum* strain ATCC 15707 (T), or a combination thereof.

In some preferred embodiments, the *Bifidobacterium longum* subsp *longum* strain *B. longum* CNCM 1-2618 (NCC 2705) is used.

DETAILED DESCRIPTION OF THE INVENTION

Composition

Figure 1:
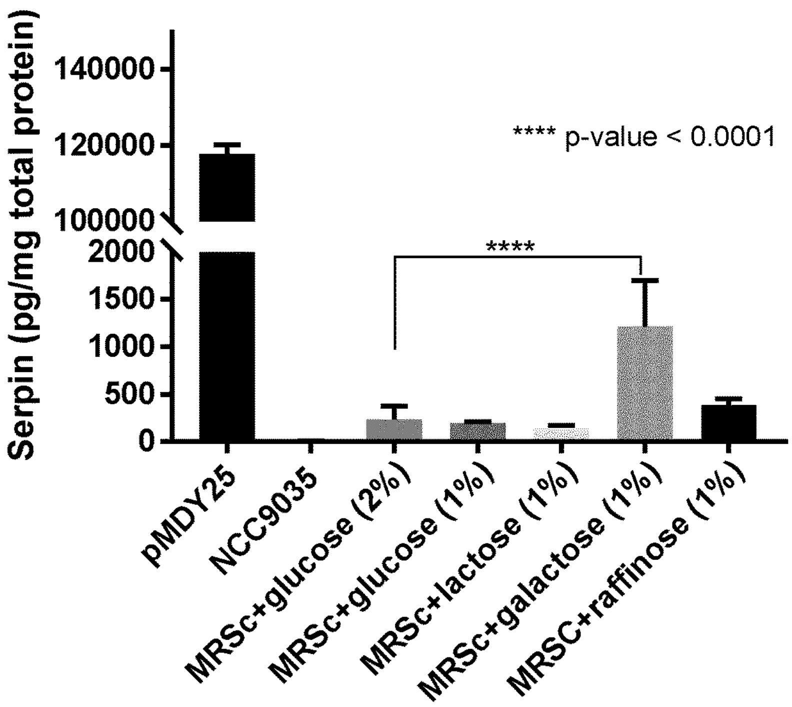
FIG. 1—Shows serpin protein levels measured in *B. longum* NCC 2705 grown for 8 h on different carbohydrates.

The composition of the present invention may be in the form of a food, a medical food, a tube feed, a nutritional composition, or a nutritional supplement. The term "nutritional supplement" refers to a product which is intended to supplement the general diet of a subject.

In one embodiment, the food is selected from milk, yoghurt, curd, cheese, fermented milks, milk based fermented products, rice based products, milk based powders, infant formulae and pet food.

The composition may be in the form of a medical food. The term "medical food" as used herein refers to a food product specifically formulated for the dietary management of a medical disease or condition. The medical food may be administered under medical supervision. The medical food may be for oral ingestion or tube feeding.

The composition may be in the form of a tube feed. The term "tube feed" refers to a product which is intended for introducing nutrients directly into the gastrointestinal tract of a subject by a feeding tube. A tube feed may be administered by, for example, a feeding tube placed through the nose of a subject (such as nasogastric, nasoduodenal, and nasojejunal tubes), or a feeding tube placed directly into the abdomen of a subject (such as gastrostomy, gastrojejunostomy, or jejunostomy feeding tube).

The composition may in the form of a pharmaceutical composition and may comprise one or more suitable pharmaceutically acceptable carriers, diluents and/or excipients.

Examples of such suitable excipients for compositions described herein may be found in the "Handbook of Pharmaceutical Excipients", 2nd Edition, (1994), Edited by A Wade and PJ Weller. Acceptable carriers or diluents for therapeutic use are well known in the pharmaceutical art, and are described, for example, in "Remington's Pharmaceutical Sciences", Mack Publishing Co. (A. R. Gennaro edit. 1985).

Examples of suitable carriers include lactose, starch, glucose, methyl cellulose, magnesium stearate, mannitol, sorbitol and the like. Examples of suitable diluents include ethanol, glycerol and water.

The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant (s), suspending agent(s), coating agent(s) and/or solubilising agent(s).

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol. Examples of suitable lubricants include sodium oleate, sodium stearate, magnesium stearate, sodium benzoate, sodium acetate, sodium chloride and the like.

Preservatives, stabilisers, dyes and even flavouring agents may be provided in the composition. Examples of preservatives include sodium benzoate, sorbic acid and esters of p-hydroxybenzoic acid. Antioxidants and suspending agents may be also used.

Nutritionally acceptable carriers, diluents and excipients include those suitable for human or animal consumption that are used as standard in the food industry. Typical nutritionally acceptable carriers, diluents and excipients will be familiar to the skilled person in the art.

The composition may be in the form of a tablet, dragee, lozenges, capsule, gel cap, powder, granule, solution, emulsion, suspension, coated particle, spray-dried particle or pill.

In an alternative embodiment the composition may be in the form of a composition for topical administration, such as a gel, cream, ointment, emulsion, suspension or solution for topical administration.

It is clear to those skilled in the art that an ideal dose will depend on the subject to be treated, its health condition, sex, age, or weight, for example, and the route of administration. The dose to be ideally used will consequently vary but can be determined easily by those of skill in the art.

However, generally, it is preferred if the composition of the present invention comprises between 106 and 1010 cfu and/or between 106 and 1010 cells of *Bifidobacterium longum* subsp *longum* per daily dose. It may also comprise between 106 and 1011 cfu and/or between 106 and 1011 cells of *Bifidobacterium longum* subsp *longum* per g of the dry weight of the composition.

*Bifidobacterium longum*

The *Bifidobacterium longum* may be any *Bifidobacterium longum* subsp *longum* strain. In some embodiments the *Bifidobacterium longum* subsp *longum* strain may be selected from *Bifidobacterium longum* subsp *longum* strain CNCM 1-2169, *Bifidobacterium longum* subsp *longum* strain CNCM 1-2171, *Bifidobacterium longum* subsp *longum* strain ATCC BAA-999 (available from Morinaga Milk Industry Co. Ltd, as BB536), *Bifidobacterium longum* subsp *longum* strain ATCC 15708, *Bifidobacterium longum* subsp *longum* strain DSM 20097, *Bifidobacterium longum* subsp *longum* strain NCI MB 8809, *Bifidobacterium longum* subsp *longum* strain CNCM 1-2618 (NCC 2705), *Bifidobacterium longum* subsp *longum* strain CNCM 1-2170, *Bifidobacterium longum* subsp *longum* strain ATCC 15707 (T), *Bifidobacterium longum* subsp *longum* strain CNCM 1-103, *Bifidobacterium longum* subsp *longum* strain CNCM 1-2334, *Bifidobacterium longum* subsp *longum* strain CNCM 1-3864, *Bifidobacterium longum* subsp *longum* strain CNCM 1-3853, or a combination thereof.

The strains have been deposited in the depositary institution indicated in the table below (Table 1), and have received the following date of deposit and accession number:

TABLE 1

| # | Depositary institution | Accession number | Date of deposit |
|---|---|---|---|
| 1 | CNCM | 1-2169 | Mar. 15, 1999 |
| 2 | CNCM | 1-2171 | Mar. 15, 1999 |
| 3 | ATCC | 15708 | <1990 |
| 4 | DSM | 20097 | <1990 |
| 5 | NCIMB | 8809 | Oct. 1, 1956 |
| 6 | CNCM | 1-2618 | Jan. 29, 2001 |
| 7 | CNCM | 1-2170 | Mar. 15, 1999 |
| 8 | ATCC | 15707 | <1990 |
| 9 | CNCM | 1-103 | Oct. 29, 1979 |
| 11 | CNCM | 1-2334 | Oct. 12, 1999 |
| 12 | CNCM | 1-3864 | Nov. 15, 2007 |
| 13 | CNCM | 1-3853 | Oct. 16, 2007 |

CNCM refers to Collection nationale de cultures de micro-organismes, Institut Pasteur, 28, rue du Dr Roux, F-75724 Paris Cedex 15, France. ATCC refers to American Type Culture Collection 10801 University Blvd., Manassas, Virginia 20110-2209, U.S.A. DSM refers to Leibniz Institute DSMZ-German Collection of Microorganisms and Cell Cultures, lnhoffenstr. 7B, D-38124 Braunschweig, Germany. NCIMB refers to NCIMB Ltd, Ferguson Building, Craibstone Estate, Buckburn, Aberdeen AB21 9YA, Scotland.

Strains 1, 2, 6, 7, 9, 11-13 have been deposited by Nestec S.A., avenue Nestle 55, 1800 Vevey, Switzerland. Since then, Nestec S.A. has merged into Societe des Produits Nestle S.A. Accordingly, Societe des Produits Nestle S.A. is the successor in title of Nestec S.A., under article 2(ix) of the Budapest Treaty. All other strains are commercially available.

In some preferred embodiments, the *Bifidobacterium longum* subsp *longum* may be selected from *Bifidobacterium longum* subsp *longum* strain CNCM 1-2169, *Bifidobacterium longum* subsp *longum* strain CNCM 1-2171, *Bifidobacterium longum* subsp *longum* strain ATCC 15708, *Bifidobacterium longum* subsp *longum* strain DSM 20097, *Bifidobacterium longum* subsp *longum* strain NCIMB 8809, *Bifidobacterium longum* subsp *longum* strain CNCM 1-2618 (NCC 2705), *Bifidobacterium longum* subsp *longum* strain CNCM 1-2170, *Bifidobacterium longum* subsp *longum* strain ATCC 15707 (T), or a combination thereof.

In some preferred embodiments, the *Bifidobacterium longum* subsp *longum* strain *B. longum* CNCM 1-2618 (NCC 2705) is used.

GOS

The present inventors have surprisingly found that galactose and galactooligosaccharides (GOS) can increase the production of serpin in bacteria of the species *Bifidobacterium longum* subsp *longum.*

The term "oligosaccharide" as used herein refers to a carbohydrate having a degree of polymerisation (DP) ranging from 2 to 20 inclusive.

"Degree of polymerisation" or "DP" refers to the total number of saccharide units in an oligo- or polysaccharide chain.

The term "galacto-oligosaccharide" as used herein refers to a non-digestible oligosaccharide comprising two or more galactose molecules. The galacto-oligosaccharides of the present invention have a DP of 2 to 20, preferably a DP of 2 to 10. Peferably at least 30% of the saccharide units are galactose units, preferably at least 50%, more preferably at least 60%, based on monomeric subunits.

Suitable galacto-oligosaccharides are commercially available, and include for example Purimune GOS (from Com-Products International), King GOS (from King Prebiotics), Vivinal GOS (from Friesland Campina), and PHGG (from Taiyo). Other suppliers of oligosaccharides include Clasado, Ingredion, Leprino, Yakult, Dextra Laboratories, Sigma-Aldrich Chemie GmbH and Kyowa Hakko Kogyo Co., Ltd. Alternatively, specific glycoslytransferases, such as galactosyltransferases may be used to produce neutral oligosaccharides.

Because of the configuration of their glycosidic bonds, galactooligosaccharides (GOS) largely resist hydrolysis by salivary and intestinal digestive enzymes. GOS are classified as prebiotics, non-digestible carbohydrates that beneficially affect the host by stimulating the growth and/or activity of beneficial bacteria in the colon.

The *Bifidobacterium longum* subsp *longum* may be cultured in a medium comprising galactose or GOS, or a mixture thereof, at a concentration of, for example, 0.02 to 5 wt %. For example, the *Bifidobacterium longum* subsp *longum* may be cultured in a medium comprising galactose or GOS, or mixtures thereof, at a concentration 0.02 to 5 wt %, 0.05 to 2 wt %, 0.1 to 1.5 wt %, or about 1 wtc1/0.

The galactose or GOS, or mixtures thereof, may be added to a conventional culture medium comprising up to 8 wt %, preferably up to 6 wt %, for example up to 4 wt %, of another sugar suitable to sustain *B. longum* growth, such as, but not limited to, glucose. The inventors have surprisingly found that galactose can induce production of serpin in *Bifidobacterium longum* subsp *longum* even when glucose is present, but only when the glucose is present at levels allowing its depletion during fermentation. Preferably the culture medium at the end of the fermentation contains less than 0.4 wt % glucose, such as from 0 wt % to 0.3 wt % glucose, for example from 0.02 wt % to 0.4 wt %, or from about 0.05 wt % to about 0.3 wt %. Conventional culture mediums suitable for growth of *B. longum* are well known to the person skilled in the art.

In one embodiment, the *Bifidobacterium longum* subsp *longum* may be cultured in a medium comprising galactose at a concentration of, 0.05 to 2 wt %, 0.1 to 1.5 wt %, or about 1 wt %, optionally in the presence of glucose at a concentration enabling its depletion until the end of the fermentation. Preferably the culture medium at the end of the fermentation contains less than 0.4 wt % glucose, such as from 0 wt % to 0.3 wt % glucose. If glucose is present, the culture medium may contain, at the end of fermentation, for example, 0.02 wt % to 0.4 wt %, or about 0.05 wt % to about 0.3 wt % glucose.

In one embodiment, the *Bifidobacterium longum* subsp *longum* may be cultured in a medium comprising GOS at a concentration of 0.05 to 2 wt %, 0.1 to 1.5 wt %, or about 1 wt %, optionally in the presence of residual glucose at a concentration of 0.02 wt % to 0.4 wt %%, or about 0.05 et % to about 0.3 wt %.

In one embodiment, galactose is used at the concentrations described above.

In one embodiment, GOS is used at the concentrations described above.

Process for Producing a Culture Powder

Strains belonging to the species *B. longum* are grown in anaerobic conditions. Fermentation methods under anaerobic conditions are commonly known. The skilled person is able to identify suitable components of the fermentation medium and to adjust fermentation conditions based on his general knowledge, depending on the microorganism to be grown. The fermentation medium typically comprises a nitrogen source such as yeast extract, a carbon source such as a sugar, various growth factors (e.g minerals, vitamins etc.) required by the microorganism and water.

A non-limiting example of a typical growth medium for *B. longum* is MRS (De Man, Rogosa and Sharpe) medium, supplemented with 0.05% of cysteine (MRSc).

The fermentation is preferably carried out in two steps, a starter fermentation being carried out prior to the main fermentation step. The fermentation medium can be different for the starter and the main fermentation or may be identical.

The second step of the process is the concentration of the biomass. This can also be carried out using methods known to the person skilled in the art, such as for example centrifugation or filtration. The total solid content of the biomass after concentration is preferably comprised between 10 and 35 wt %, preferably between 14 and 35 wt %, based on the total dry weight of the biomass (i.e. of the total amount of fermentation medium and produced microorganism).

Optionally, the concentration may be preceded or combined with a washing step to remove residues of the fermentation medium and/or compounds produced during fermentation. For example, washing may be performed by concentrating biomass, re-suspending the concentrated biomass in a buffer, such as a phosphate buffer, or a similar composition and re-concentrating the biomass.

For example, the process described in WO2017/001590, which is entirely incorporated by reference, can be applied.

Combination

In one aspect of the present invention, there is provided a combination of (i) a *Bifidobacterium longum* subsp *longum* and (ii) galactose or GOS, or a combination thereof.

As used herein, the term "combination" refers to the combined administration of *Bifidobacterium longum* subsp *longum* and galactose or GOS, or a combination thereof, wherein the *Bifidobacterium longum* subsp *longum* and the galactose and/or GOS may be administered simultaneously or sequentially.

As used herein, the term "simultaneous" or "simultaneously" is used to mean that the two agents are administered concurrently, i.e. at the same time.

The term "sequential" or "sequentially" is used to mean that the two agents are administered one after the other, wherein either the *Bifidobacterium longum* subsp *longum* or the galactose or GOS, or the combination thereof, may be administered first.

The agents may be administered either as separate formulations or as a single combined formulation.

When the compounds are co-formulated, i.e. in the same composition or formulation, they can only be administered simultaneously. When the compounds are formulated in separate compositions or formulations, they can be administered simultaneously or sequentially. Simultaneous administration of the agents in the same formulation or in separate formulations can also be described as the co- or joint administration of the two compounds.

In one embodiment, *Bifidobacterium longum* subsp *longum* and the galactose or GOS, or a combination thereof are in admixture. In another embodiment, the *Bifidobacterium longum* subsp *longum* and galactose or GOS, or a combination thereof, are present in the form of a kit comprising a preparation of the two agents and, optionally, instructions for the simultaneous or sequential administration of the preparations to a subject in need thereof.

Treatment

The *Bifidobacterium longum* subsp *longum* strains produced according to the present invention, or a composition comprising the same, may be for use in the treatment or prevention of gluten related disorders or conditions involving a reduced activity of serine protease inhibitors.

For example the *Bifidobacterium longum* subsp *longum* produced according to the present invention, or a composition comprising the same, may be for use in the treatment or prevention of inflammatory bowel disease, celiac disease, non-celiac gluten sensitivity, gluten ataxia, dermatitis herpetiformis and wheat allergy.

Preferably the disease is a gluten-related disorder. Gluten-related disorders encompass diseases triggered by gluten. The terms "conditions related to gluten sensitivity" and "gluten-related disorders" are used interchangeably herein. Gluten-related disorders include celiac disease, non-celiac gluten sensitivity, gluten ataxia, dermatitis herpetiformis and wheat allergy.

Celiac Disease

Celiac disease is one of the most common immune mediated disorders. It is a worldwide condition and is prevalent especially in the United States and Europe where around 1% of subjects had positive antibody tests. Celiac disease is a complex disorder which arises from a complicated interaction among various immunologic, genetic, and environmental factors. It is triggered by the digestion of wheat gluten and other related cereal proteins such as rye and barley proteins. Symptoms linked with celiac disease are growth retardation, irritability and pubertal delay in children and many gastrointestinal symptoms like discomfort, diarrhoea, occult stool, steatorrhea flatulence.

Clinical evidence shows class II human leukocyte antigens (HLA-DQII), which strongly relate with celiac disease pathology, are expressed in about 95% of celiac disease patients. In the intestinal lumen, gluten protein are partially digested, forming proteolytic-resistant 33-mer gluten peptide. After crossing the small intestinal barrier, they are deamidated by transglutaminase 2 (TG2) with negative charges (Sollid, 2000, Annual review of immunology, 18(1), 53-81), which then bind to the positively charged binding sites of HLA-DQ2.5/8 (Dieterich et al., 1997, Nature medicine, 3(7), 797-801). HLA-DQ2.5/8 displaying those specific gluten peptides signals to helper T cells and other immune cells causing further damage in the small intestine. Antibodies against gluten proteins and autoantibodies to connective tissue components (TG2) are also associated with celiac disease progression (Alaedini & Green, 2005, Annals of internal medicine, 142(4), 289-298).

Non-Celiac Gluten Sensitivity

Non-celiac gluten sensitivity (also designated as non-celiac wheat sensitivity) is an emerging condition. It is defined as a clinical entity induced by the ingestion of gluten leading to intestinal and/or extraintestinal symptoms which could be improved by removing the gluten-containing foodstuff from the diet (Lundin & Alaedini, 2012). The pathogenesis of non-celiac gluten sensitivity is not yet well understood. It has been shown that except for gliadin (main cytotoxic antigen of gluten), other proteins/peptides present in gluten and gluten-containing cereals (wheat, rye, barley, and their derivatives) may play a role in the development of symptoms. Non-celiac gluten sensitivity is the most common syndrome of gluten-related disorders with prevalence rates between 0.5-13% in the general population (Catassi et al., 2013, Nutrients, 5(10), 3839-385). The diagnosis of non-celiac gluten sensitivity is made by exclusion of other gluten-related disorders.

Dermatitis Herpetiformis

Dermatitis herpetiformis is a chronic blistering skin autoimmune condition, characterized by the presence of skin lesions that have an extensive and symmetrical distribution, predominating in areas of greater friction, and affecting mainly both elbows, knees, buttocks, ankles, and may also affect the scalp and other parts of the body. The lesions are vesicular-crusted and when they flake 25 off, they evolve to pigmented areas or a chromic and intense burning, itchy and blistering rash.

The age of onset is variable. It may start in children and adolescents but can also affect individuals of both sexes indistinctly at any age of their lives.

People with dermatitis herpetiformis have different degrees of intestinal involvement, ranging from milder mucosal lesions to the presence of villous atrophy.

Wheat Allergy

Gastrointestinal symptoms of wheat allergy are similar to those of celiac disease and non-celiac gluten sensitivity, but there is a different interval between exposure to wheat and onset of symptoms. Wheat allergy has a fast onset (from minutes to hours) after the consumption of food containing wheat and can lead to anaphylaxis.

Gluten Ataxia

Gluten ataxia is a gluten-related disorder. With gluten ataxia, damage takes place in the cerebellum, the balance center of the brain that controls coordination and complex movements like walking, speaking and swallowing. Gluten ataxia is the single most common cause of sporadic idiopathic ataxia. It accounts for 40% of ataxias of unknown origin and 15% of all ataxias.

Gluten ataxia is an immune-mediated disease triggered by the ingestion of gluten in genetically susceptible individuals. It should be considered in the differential diagnosis of all patients with idiopathic sporadic ataxia. The effectiveness of the treatment depends on the elapsed time from the onset of the ataxia until diagnosis. The death of neurons in the cerebellum as a result of gluten exposure of the subject is irreversible.

Early diagnosis and treatment with a gluten free diet can improve ataxia and prevent its progression. Less than 10% of people with gluten ataxia present any gastrointestinal symptom, yet about 40% have intestinal damage. Sensitive markers of gluten ataxia include anti-gliadin antibodies. Immunoglobulin A (IgA) deposits against transglutaminase 2 (TG2) in the small bowel and at extraintestinal sites are proving to be additionally reliable.

Administration

The *Bifidobacterium longum* subsp *longum* or composition described herein are preferably administered enterally.

Enteral administration may be oral, gastric, and/or rectal.

In general terms, administration of the combination or composition described herein may, for example, be by an oral route or another route into the gastro-intestinal tract, for example the administration may be by tube feeding.

In an alternative embodiment administration of the combination or composition described herein may be topical administration.

The subject may be a mammal such as a human, canine, feline, equine, caprine, bovine, ovine, porcine, cervine and primates. Preferably the subject is a human.

Preferred features and embodiments of the invention will now be described by way of non-limiting examples.

The practice of the present invention will employ, unless otherwise indicated, conventional techniques of chemistry, biochemistry, molecular biology, microbiology and immunology, which are within the capabilities of a person of ordinary skill in the art. Such techniques are explained in the literature. See, for example, Sambrook, J., Fritsch, E. F. and Maniatis, T. (1989) Molecular Cloning: A Laboratory Manual, 2nd Edition, Cold Spring Harbor Laboratory Press; Ausubel, F. M. et al. (1995 and periodic supplements) Current Protocols in Molecular Biology, Ch. 9, 13 and 16, John Wiley & Sons; Roe, B., Crabtree, J. and Kahn, A. (1996) DNA Isolation and Sequencing: Essential Techniques, John Wiley & Sons; Polak, J. M. and McGee, J. O'D. (1990) In Situ Hybridization: Principles and Practice, Oxford University Press; Gait, M. J. (1984) Oligonucleotide Synthesis: A Practical Approach, IRL Press; and Lilley, D. M. and Dahlberg, J. E. (1992) Methods in Enzymology: DNA Structures Part A: Synthesis and Physical Analysis of DNA, Academic Press. Each of these general texts is herein incorporated by reference.

EXAMPLES

Example 1—*B. longum* CNCM 1-2618 (NCC 2705) Serpin Induction by Galactose

*B. longum* strain CNCM 1-2618 (NCC 2705) was grown in Biolector (growth conditions—anaerobic, 37 00) in MRS+5 mM L-cysteine (MRSc) base without sugar, to which different carbohydrates were added.

48-well microtiter plate with pH sensor and dissolved oxygen (DO) sensor were used to culture the strains in Biolector (m2p-labs Aachen, Germany). It was continuously shaken to prevent bacteria aggregation for 8 h. Cultures were harvested by centrifugation and supernatant was removed. Pellet was resuspended in PBS supplemented with halt protease inhibitor (Sigma) and lysed using glassbeads. Lysate containing both soluble and insoluble material was then collected.

Total protein content was measured using Pierce BCA kit (Thermofisher) and serpin protein concentration was determined using ELISA.

As shown in FIG. 1, galactose was shown to increase *B. longum* NCC 2705 serpin protein levels, as compared to all other sugars tested.

Example 2—*B. longum* CNCM 1-2618 (NCC 2705) Serpin Induction by Galactose in the Presence of Glucose

*B. longum* NCC 2705 was cultured in Biolector (as described in Example 1) in a base of MRSc without sugar, with the addition of different glucose & galactose ratios, to a final concentration of 1%. Cultures were collected after 18 h of growth and analyzed for total & serpin protein levels (as described in Example 1).

Figure 2:
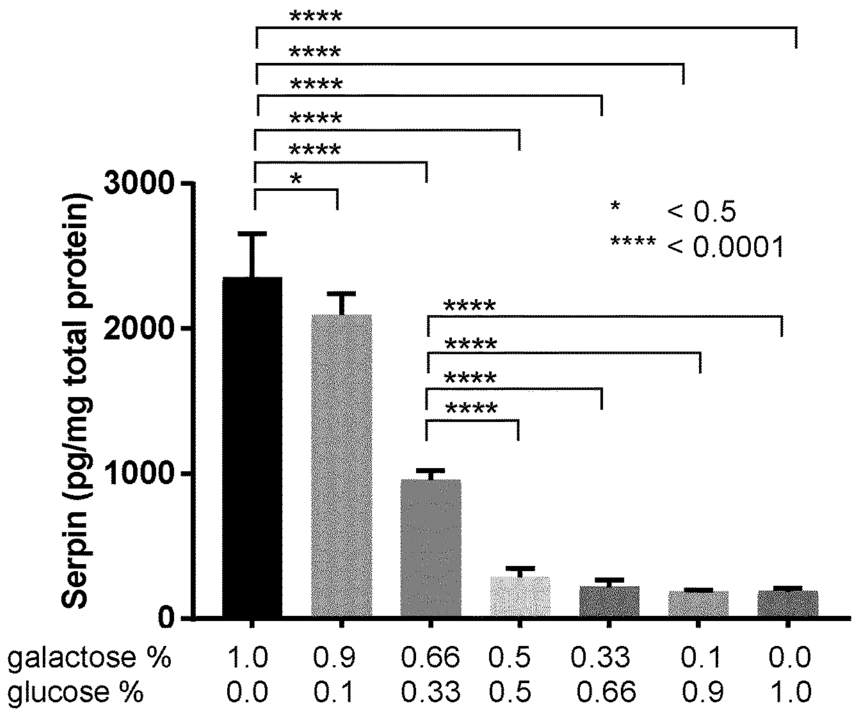
FIG. 2—Shows serpin protein levels measured in *B. longum* NCC 2705 grown on different ratios of glucose & galactose.

Results (FIG. 2) show that galactose can induce production of serpin in *B. longum* NCC 2705 even when glucose is present, but only when the glucose is present at level at which it is depleted during fermentation. In the model system used in this example, addition of 0.3% was the maximal addition rate of glucose allowing its depletion during the fermentation (data not shown). Accordingly, glucose concentration in the fermentation system/growth medium should be kept low relative to the galactose concentration.

Example 3—*B. longum* NCC 2705 Serpin Induction by Galactooligosaccharides (GOS)

Figure 3:
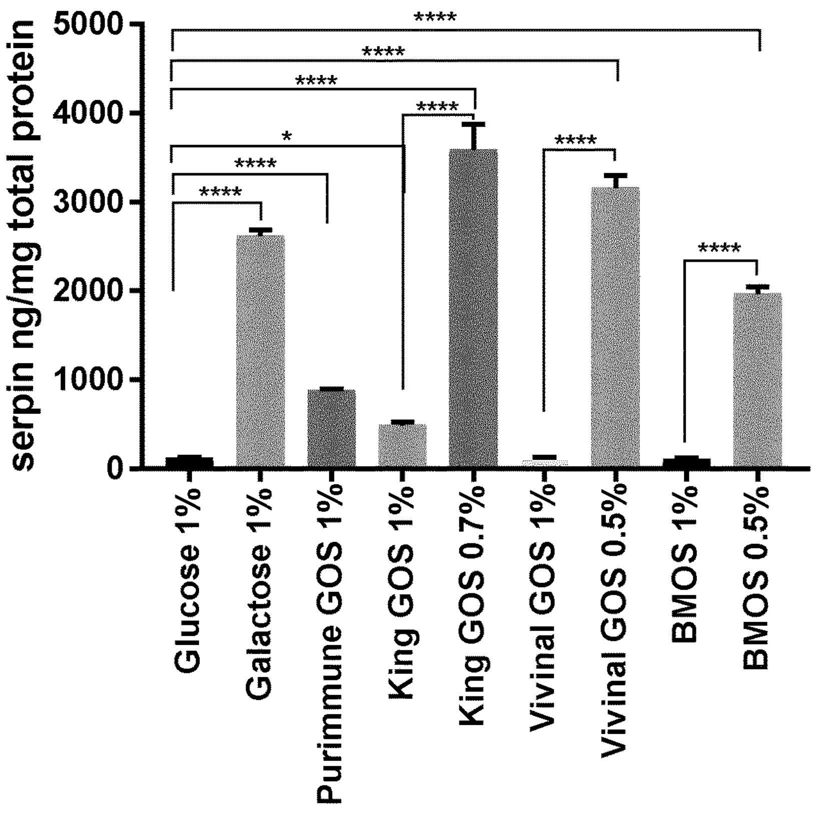
FIG. 3—Shows serpin protein levels measured in *B. longum* NCC 2705 grown for 8 h on GOS.
Figure 4:
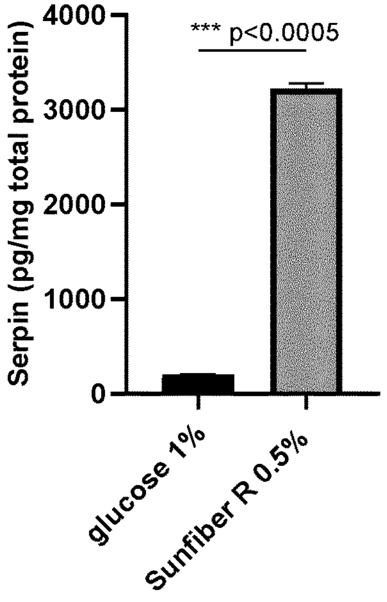
FIG. 4—Shows the Influence of (Partially Hydrolyzed Guar Gum (PHGG)) on serpin level of *B. longum* NCC 2705.

*B. longum* NCC 2705 was grown on an MRSc base without sugar, with addition of different commercially available galactooligosaccharides (GOS) at different concentrations. Cultures were grown as indicated previously (see Example 1) for 18 h and harvested. Obtained pellets were analyzed for total and serpin protein content (see Example 1). The tested commercial GOS were Purimune GOS (from CornProducts International), King GOS (GDS-700-P from King Prebiotics), Vivinal GOS syrup (from DOMO), BMOS (Bovine Milk Oligosaccharides, from Nestle), Sunfiber R (Partially Hydrolyzed Guar Gum; from Taiyo GmbH) Purimmune GOS, King GOS, Vivinal GOS and BMOS supported the growth of *B. longum* NCC 2705. As shown in FIG. 3, these GOS could significantly increase the levels of serpin protein in *B. longum* NCC 2705. As the commercially available GOS all contain residual sugars (mainly glucose and lactose), the concentration at which they are used should to be adjusted so that those residual sugars are present at a level that is depleted during fermentation. Sunfiber R alone only partially supported the growth of *B. longum* NCC 2705 (data not shown), however, like the other tested GOS, it was able to increase significantly the levels of serpin protein in *B. longum* NCC 2705 (FIG. 4).

Example 4—*B. longum* Subsp. *Longum Serpin* Induction by Galactose

The serpin encoding gene and its surrounding is highly conserved within the *B. longum* subsp. *longum* species. Strains of *B. longum* subsp. *longum* were selected to represent the entire span of the genetic phylogenetic tree (Table 2). All strains were cultured in Biolector (according to example 1) in a MRSc base without sugar, to which 1% glucose, 1% galactose or a mix of glucose & galactose (respectively 0.2 & 0.8%) was added. Cultures were grown for 18 h and harvested. Obtained pellets were further analyzed for total and serpin protein content (see example 1).

TABLE 2 list of *B. longum* subsp. *longum* strains tested and the homology of their serpin gene to BL0108 (*B. longum* NCC 2705 serpin encoding gene).

| Strain no | % ID to BL0108 (NCC 2705 serpin) |
|---|---|
| NCC 2705 (CNCM I-2618) | 100.00 |
| ATCC 15707 (T) | 99.78 |
| CNCN I-2171 | 99.79 |
| ATCC BAA-999 | 99.78 |
| ATCC 15708 | 99.57 |
| DSM 20097 | 97.42 |
| NCIMB 8809 | 99.79 |
| CNCM I-2170 | 100 |

Figure 5:
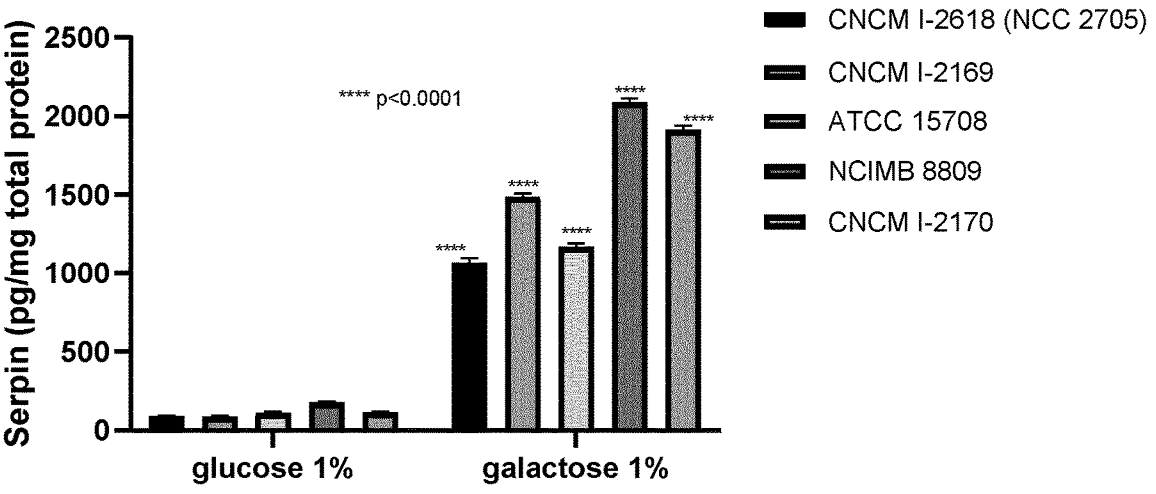
FIG. 5—Shows the influence of galactose on serpin levels of *B. longum* subsp. *longum* strains able to grow on galactose. Values represent protein levels normalized by total amount of protein in each sample.
Figure 6:
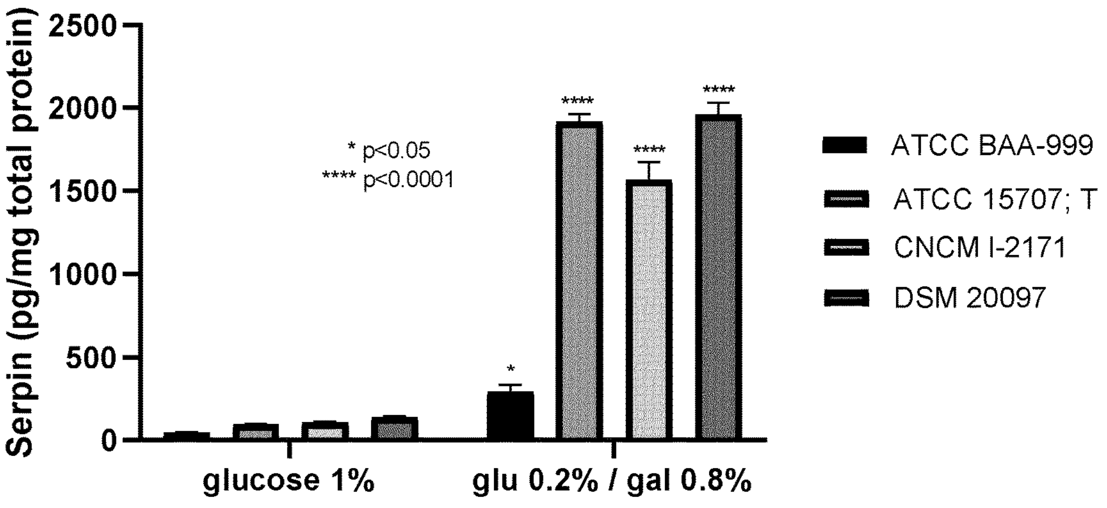
FIG. 6—Shows the influence of galactose on serpin levels of *B. longum* subsp. *longum* strains unable to grow on galactose alone. Values represent protein levels normalized by total amount of protein in each samples.

Not all strains of *B. longum* subsp. *longum* were able to grow on galactose as sole carbohydrate source. However, as shown in FIGS. 5 and 6, despite this, importantly serpin protein levels were increased in all *B. longum* subsp. *longum* strains in presence of galactose, meaning that the induction capacity of galactose is not dependent on its capacity to be metabolized for growth.

Example 5—*B. longum* Serpin Induction by Galactose

Serpin is furthermore conserved within a restricted number of Bifidobacteria species (Turroni, F. et al. Characterization of the serpin-encoding gene of *Bifidobacterium breve* 210B. *Appl Environ Microbiol* 76, 3206-3219, doi:10.1128/AEM.02938-09 (2010)). Strains belonging to these species (Table 3) were cultured in Biolector (see example 1) in a MRSc base without sugar, to which 1% glucose, 1% galactose was added. As well, on top of 1% glucose, 0.05 mg/ml of papain (from Worthington) was tested, as it was previously demonstrate to induce serpin in *B. breve*. Cultures were grown for 18 h and harvested. Obtained pellets were further analyzed for total and serpin protein content (see example 1).

TABLE 3 list of strains used and the homology of their serpin gene to BL0108 (*B. longum* NCC 2705 serpin encoding gene).

| Species | Strain no | ID to BL0108 (NCC 2705 serpin) |
|---|---|---|
| *B. longum* subsp. *longum* | NCC 2705 (CNCM I-2618) | 100.00 |
| *B. longum* subsp. *longum* | ATCC 15707 (T) | 99.78 |
| *B. longum* subsp. *infantis* | ATCC 15697 (T) | 94.85 |
| *B. longum* subsp. *suis* | ATCC 27533 (T) | 92.70 |
| *B. breve* | ATCC 15700 (T) | 93.35 |

Figure 7:
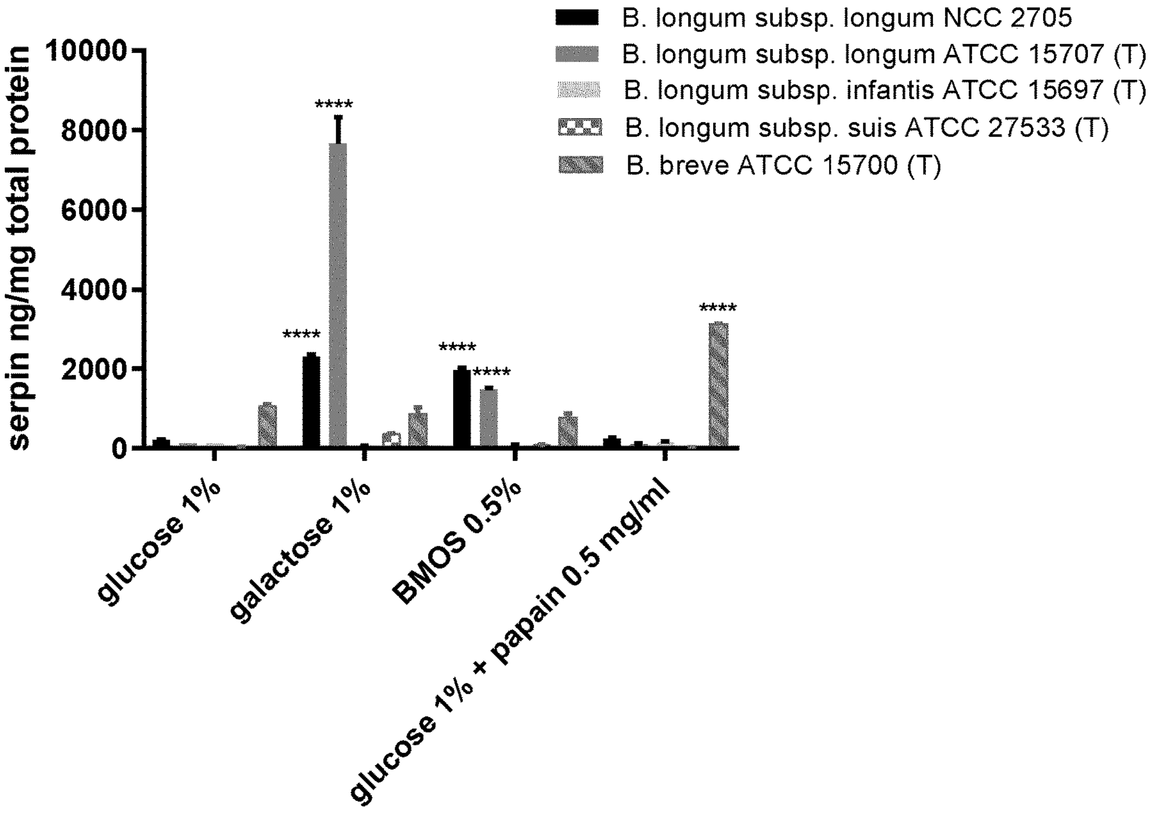
FIG. 7—Shows the Influence of galactose, GOS and papain on different bifidobacteria strains possessing a serpin encoding gene. Values represent protein levels normalized by total amount of protein in each sample.

As shown in FIGS. 5-7, all tested *B. longum* subsp. *longum* strains responded to galactose and showed a significant serpin protein increase. Whereas, on the contrary, none of the *B. breve* ATCC 15700 (T), *B. longum* subsp *infantis* nor *B. longum* subsp suis strains were induced by galactose. Papain, which was previously shown to induce *B. breve* serpin, did not increase serpin levels in *B. longum* subsp. *longum* cultures, but did in the *B. breve* ATCC 15700 (T) strain. The two strains belonging to *B. longum* subsp *infantis* and suis respectively were neither induced by galactose, nor by papain (FIG. 7).

The invention claimed is:

1. A method for increasing serpin protein levels in *Bifidobacterium longum* subsp *longum*, the method comprising:

fermenting *Bifidobacterium longum* subsp *longum* in a culture medium comprising galactose and less than 0.3 wt % glucose, and the culture medium does not contain any beta-galactooligosaccharides (GOS), wherein a level of residual glucose in the culture medium at the end of the fermenting is at a concentration of 0.05 wt % to 0.3 wt %; and measuring serpin protein concentration after the fermenting, wherein the serpin protein levels after fermenting the *Bifidobacterium longum* subsp *longum* in the culture medium are increased compared to a culture medium comprising greater than 0.3 wt % glucose.

2. The method of claim 1, wherein the *Bifidobacterium longum* subsp *longum* is selected from the group consisting of *Bifidobacterium longum* subsp *longum* strain CNCM I-2169, *Bifidobacterium longum* subsp *longum* strain CNCM I-2171, *Bifidobacterium longum* subsp *longum* strain ATCC BAA-999, *Bifidobacterium longum* subsp *longum* strain ATCC 15708, *Bifidobacterium longum* subsp *longum* strain DSM 20097, *Bifidobacterium longum* subsp *longum* strain NCIMB 8809, *Bifidobacterium longum* subsp *longum* strain CNCM I-2618 (NCC 2705), *Bifidobacterium longum* subsp *longum* strain CNCM I-2170, *Bifidobacterium longum* subsp *longum* strain ATCC 15707 (T), and a combination thereof.

3. A method of fermenting *Bifidobacterium longum* subsp *longum*, the method comprising:

fermenting the *Bifidobacterium longum* subsp *longum* in a culture medium comprising galactose and less than 0.3 wt % glucose, and the culture medium does not contain any beta-galactooligosaccharides (GOS), wherein a level of residual glucose in the culture medium at the end of the fermenting is at a concentration of 0.05% to 0.3 wt %; and measuring serpin protein concentration after the fermenting, wherein the serpin protein levels after fermenting the *Bifidobacterium longum* subsp *longum* in the culture medium are increased compared to a culture medium comprising greater than 0.3 wt % glucose.

4. The method of claim 3, wherein the *Bifidobacterium longum* subsp *longum* is selected from the group consisting of *Bifidobacterium longum* subsp *longum* strain CNCM I-2169, *Bifidobacterium longum* subsp *longum* strain CNCM I-2171, *Bifidobacterium longum* subsp *longum* strain ATCC BAA-999, *Bifidobacterium longum* subsp *longum* strain ATCC 15708, *Bifidobacterium longum* subsp *longum* strain DSM 20097, *Bifidobacterium longum* subsp *longum* strain NCIMB 8809, *Bifidobacterium longum* subsp *longum* strain CNCM I-2618 (NCC 2705), *Bifidobacterium longum* subsp *longum* strain CNCM I-2170, *Bifidobacterium longum* subsp *longum* strain ATCC 15707 (T), *Bifidobacterium longum* subsp *longum* strain CNCM I-103, *Bifidobacterium longum* subsp *longum* strain CNCM I-2334, *Bifidobacterium longum* subsp *longum* strain CNCM I-3864, *Bifidobacterium longum* subsp *longum* strain CNCM I-3853, and a combination thereof.

5. A method of treating celiac disease, non-celiac gluten sensitivity, gluten ataxia, dermatitis herpetiformis, or wheat allergy in an individual in need thereof, the method comprising administering to the individual a composition comprising *Bifidobacterium longum* subsp *longum* and galactose, wherein the composition does not contain any beta-galactooligosaccharides (GOS), wherein the composition comprising the *Bifidobacterium longum* subsp *longum* and the galactose has been subjected to fermentation, and the composition contains 0.05 wt % to 0.3 wt % residual glucose at the end of the fermentation and wherein the composition increases serpin protein levels in the *Bifidobacterium longum* subsp *longum*.

6. The method of claim 5, wherein the *Bifidobacterium longum* subsp *longum* is selected from the group consisting of *Bifidobacterium longum* subsp *longum* strain CNCM I-2169, *Bifidobacterium longum* subsp *longum* strain CNCM I-2171, *Bifidobacterium longum* subsp *longum* strain ATCC BAA-999, *Bifidobacterium longum* subsp *longum* strain ATCC 15708, *Bifidobacterium longum* subsp *longum* strain DSM 20097, *Bifidobacterium longum* subsp *longum* strain NCIMB 8809, *Bifidobacterium longum* subsp *longum* strain CNCM I-2618 (NCC 2705), *Bifidobacterium longum* subsp *longum* strain CNCM I-2170, *Bifidobacterium longum* subsp *longum* strain ATCC 15707 (T), *Bifidobacterium longum* subsp *longum* strain CNCM I-103, *Bifidobacterium longum* subsp *longum* strain CNCM I-2334, *Bifidobacterium longum* subsp *longum* strain CNCM I-3864, *Bifidobacterium longum* subsp *longum* strain CNCM I-3853, and a combination thereof.

7. The method of claim 1, further comprising isolating the medium after culturing.

8. The method of claim 1, further comprising isolating the biomass after culturing.

9. A method of treating celiac disease, non-celiac gluten sensitivity, gluten ataxia, dermatitis herpetiformis, or wheat allergy in an individual in need thereof, the method comprising administering to the individual a composition comprising the isolated culture medium of claim 7 or the isolated biomass of claim 8.

10. The method of claim 1, wherein the culture medium comprises the galactose at a concentration of 0.02 to 5 wt %.

11. The method of claim 3, wherein the culture medium comprises the galactose at a concentration of 0.02 to 5 wt %.

12. The method of claim 3, wherein the serpin protein concentration is measured using ELISA.

13. The method of claim 3, further comprising measuring total protein content after the fermenting.

* * * * *